United States Patent [19]

Pandey

[11] Patent Number: 5,378,332
[45] Date of Patent: Jan. 3, 1995

[54] AMPEROMETRIC FLOW INJECTION ANALYSIS BIOSENSOR FOR GLUCOSE BASED ON GRAPHITE PASTE MODIFIED WITH TETRACYANOQUINODIMETHANE

[75] Inventor: Prem C. Pandey, Gaithersburg, Md.

[73] Assignee: The United States of America as represented by the Secretary of Commerce, Washington, D.C.

[21] Appl. No.: 46,187

[22] Filed: Apr. 14, 1993

[51] Int. Cl.$^6$ ............................................. G01N 27/26
[52] U.S. Cl. ............................... 204/153.12; 204/403; 204/409; 204/291; 435/817
[58] Field of Search .................... 204/403, 409, 153.12, 204/291; 435/817; 128/635

[56] References Cited

U.S. PATENT DOCUMENTS 5,089,112  2/1992  Skotheim et al. .................... 204/403
5,240,571  8/1993  Heineman et al. .............. 204/153.12

OTHER PUBLICATIONS

"A Glucose Sensor Utilizing Tetracyanoquinodimethane as a Mediator", S. P. Hendry and A. P. F. Turner, *Horm Metab. Res.*, (Suppl.) 20, pp. 37–40 (1988) No month available at present time.
"Amperometric Biosensors for Glucose Based on Carbon Paste Modified Electrodes", *Talanta*, vol. 38, No. 1, Jan. 1991; A. Amine et al.
"Enzyme Packed Bed System for the On–Line of Glucose, Glutamate, and Lactate in Brain Microdialysate", *Analytical Chemistry*, Sep. 1992; Martyn G. Boutelle et al.
"A New Class of Amperometric Biosensor Incorporating a Polymer Electron–Transfer Mediator", *Journal of the American Society*, vol. III, 1989 pp. 3482–3484 No month available at present time.
"Graphite Paste–Based Enzymatic Glucose Electrode for Flow Injection Analysis", *The Analyst*, vol. 113, No. 5, May 1988; Wojciech Matuszeski et al.
"Biocatalytic Oxidation of Glucose on the Conductive Charge Tranfer Complexes", *Bioelectrochemistry and Bioenergetics*, 8 (1981) pp. 103–113, vol. 128 No month available at present time.

*Primary Examiner*—Kathryn Gorgos
*Assistant Examiner*—Bruce F. Bell
*Attorney, Agent, or Firm*—Lowe, Price, LeBlanc & Becker

[57] ABSTRACT

A biosensor system using flow injection analysis (FIA) for the analysis of glucose in human serum. The system utilizes a sensor in which the enzyme glucose oxidase (GOD) is incorporated into graphite paste modified with tetracyanoquinodimethane (TCNQ). TCNQ acts as an efficient mediator for oxidation of the reduced enzyme at 200 mV vs Ag/AgCl. The sensor provides a linear response to glucose over a wide concentration range. The flow injection analysis system has a detection limit of 200 nmol glucose using a 100 µl sample and as been demonstrated to be stable after 800 consecutive sample injections.

19 Claims, 4 Drawing Sheets

AMPEROMETRIC FLOW INJECTION ANALYSIS BIOSENSOR FOR GLUCOSE BASED ON GRAPHITE PASTE MODIFIED WITH TETRACYANOQUINODIMETHANE

TECHNICAL FIELD

The present invention relates biosensors. More particularly, the present invention relates to biosensors and flow injection analysis systems which incorporate biosensors.

BACKGROUND ART

Electrochemical biosensors have wide practical application in clinical assays, environmental monitoring and process control because they offer excellent sensitivity, fast response, and high selectivity. In addition, they can be easily miniaturized and are inexpensive.

Amperometric response of biosensors for glucose measurement is based on probing of an enzymic reaction either by oxidation of hydrogen peroxide or by the electron exchange from the active center of the redox enzyme. The amperometric signal obtained by the electron exchange from the active center of the enzyme and electrode surface increases the selectivity and sensitivity of analysis considerably since the selective inherent properties of the enzyme are monitored directly. The electron exchange from the active center of an enzyme like glucose oxidase to the electrode surface is facilitated by incorporating electron transfer relays between the active center of the enzyme and electrode surface.

There are a number of reports on the use of organic metals including salts of tetracyanoquinodimethane (TCNQ) as an efficient electrocatalyst for the direct electron exchange from the active center of enzymes. Cenas and Kulys (*Bioelectrochem. Bioenerg.* 8, 103 (1981)) report that oxidation of redox enzymes at the surface of organic metals proceeds through a mediatory way. They express the current of an enzyme electrode in terms of mediator concentration produced during the slight dissolution of the organic metal salts on the surface of the electrode. Cenas and Kulys (*J. Electroanal. Chem.* 128, 103 (1981)) have demonstrated that TCNQ can promote electron transfer between glucose oxidase (GOD) and an electrode.

Considering previous works, Hendry and Turner (*Horm. Metab. Res.* (Suppl.) 20, 37 (1988)) have developed a glucose sensor which utilizes TCNQ as a mediator. However, the sensor suffers from a number of disadvantages including a short half-life of the electrode (i.e., 1–1.5 h), which may be attributed to either loss of enzyme activity, loss of enzyme, or leaching of TCNQ from the electrode, and a limited linear range of the calibration curve (i.e., anodic current is linear up to 20 mM glucose and nonlinear up to 75 mM).

Incorporation of mediators with redox proteins has attracted considerable attention in the development of amperometric enzyme electrodes for glucose. Accordingly, many different classes of redox-active molecules have been characterized as mediators.

Recent reports (Amine et al, *Talanta* 38, 107 (1991); Hale et al, *J. Am. Chem. Soc.* 111, 3482 (1989); Matuszewski et al, *Analyst* 113, 735 (1988)) show that GOD alone, GOD-linked mediator, or GOD and a mediator can be incorporated into a graphite/carbon paste electrode (graphite particles suspended in Nujol oil) (CPE), which results in an enzyme electrode with enhanced mechanical and electrochemical stability. The extended linearity of the sensor resulting is attributed to diffusion-limited conditions through and within the oily electrode interface. However, the limited electrode stability (8 days) is related to progressive leaching out of the mediator from the electrode (Amine et al, *Talanta* 38, 107 (1991).

Amperometric biosensors have been employed in batch type reactor systems for detecting glucose. However, flow-injection analysis (FIA) for the simultaneous determination of several components in very small sample volumes has wider application, because flow-injection systems allow well-defined and highly reproducible concentration transient at detector sites and can be operated in a variety of flow-injection modes.

Several flow-injection analysis systems which incorporate immobilized GOD for the analysis of glucose based on electrochemical detection and chemiluminometric determination are known. The electrochemical mode of detection in such systems is based on the measurement of electron-exchange from the anodic oxidation of hydrogen peroxide produced by the enzymatic reaction of GOD.

Recently a flow-injection analysis system for the on-line measurement of glucose, glutamate, and lactate in brain microdialysate has been described (Boutelle et al, *Anal. Chem.*, 64, 1790 (1992). In this system the enzyme horseradish peroxidase is regenerated by the oxidation of two ferrocene species present in a buffer which is pumped through a packed bed.

The present invention is directed to a flow-injection analysis (FIA) system which incorporates a biosensor for glucose which provides a wide linear dynamic range and good mechanical and electrochemical stability.

DISCLOSURE OF THE INVENTION

It is accordingly one object of the present invention to provide a biosensor.

Another object of the present invention is to provide a biosensor which is characterized by a wide linear dynamic range and good mechanical and electrochemical stability.

It is a further object of the present invention to provide a biosensor having an electrode which include an enzyme and an electron-transfer mediator.

A further object of the present invention is to provide a flow-injection analysis system which incorporates a biosensor.

A still further object of the present invention is to provide a method of detecting glucose in plasma samples.

A still further object of the present invention is to provide a method of detecting glucose in plasma samples which utilizes flow-injection analysis.

According to these and further objects of the present invention which will become apparent as the description thereof proceeds, the present invention provides an electrode for a biosensor which comprises a homogeneous composition of between about 8 to 15 weight percent of a redox enzyme, between about 28 to 35 weight percent of an electron-transfer mediator, between about 28 to 35 weight percent graphite powder, and between about 23 to 30 weight percent of a mineral oil.

The present invention further provides a flow-injection analysis system which includes an enzyme electrode for the electrochemical cell which comprises a homogeneous composition of between about 9 to 12 weight percent of a redox enzyme, between about 30 to 33 weight percent of an electron-transfer mediator, between about 30 to 33 weight percent graphite powder, and between about 24 to 28 weight percent of a mineral oil.

In addition, the present invention provides a method of measuring glucose concentration in a sample which involves:

providing a sample fluid containing glucose;

providing an electrochemical cell having a working electrode which comprises a homogeneous composition of between about 8 to 15 weight percent of glucose oxidase, between about 28 to 35 weight percent of tetracyanoquinodimethane, between about 28 to 35 weight percent graphite powder and between about 23 to 30 weight percent of mineral oil;

supplying the sample fluid to the electrochemical cell; and measuring glucose concentration in the sample fluid by means of said electrochemical cell.

BRIEF DESCRIPTION OF DRAWINGS

The present invention will be described with reference to the attached drawings which are given by way of non-limiting examples only, in which.

BEST MODE FOR CARRYING OUT THE INVENTION

Figure 1:
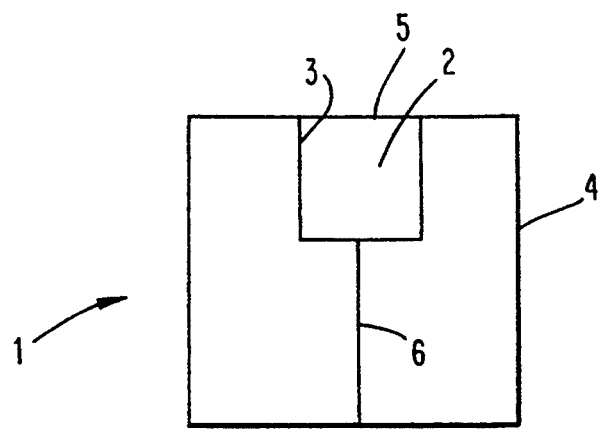
FIG. 1 is a schematic diagram of a biosensor according to the present invention.
Figure 2:
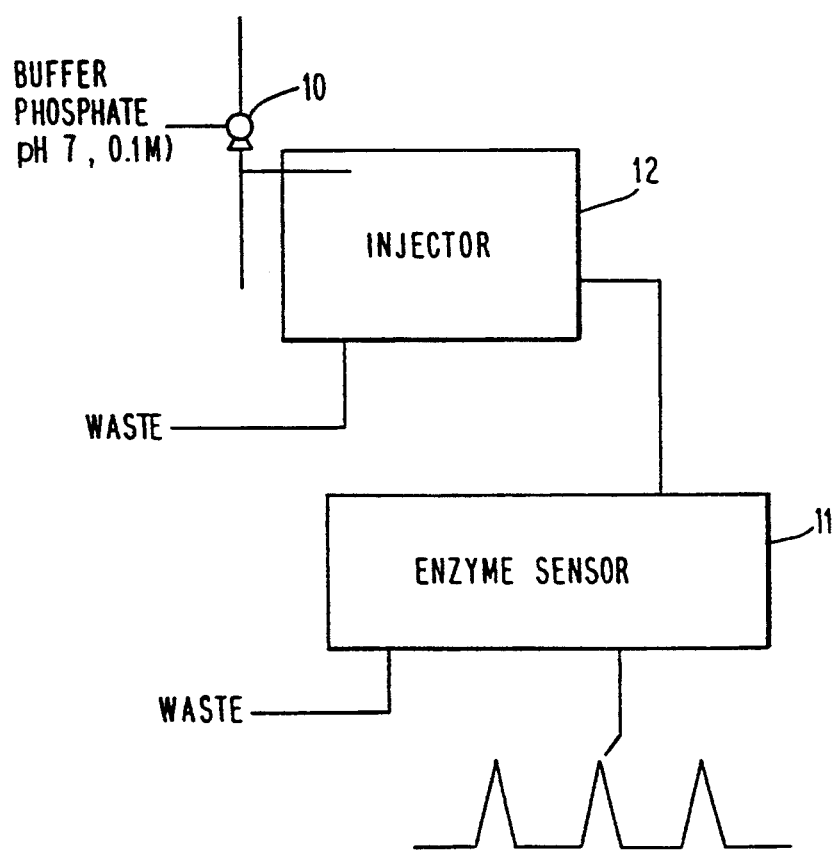
FIG. 2 is a schematic diagram of a flow-injection analysis biosensor according to the present invention.

The present invention is directed to a biosensor for glucose which incorporates GOD and TCNQ as a electron-transfer mediator into graphite paste at the surface of an electrochemical detector. The biosensor provides a wide linear dynamic range and good mechanical and electrochemical stability.

The present invention is also directed to a flow-injection analysis system which incorporates a biosensor suitable for glucose analysis in human serum samples with a simple FIA mode. The FIA system of the present invention provides for the regeneration of GOD and TCNQ at the sites of enzymatic reaction. The sensor has been utilized for the analysis of glucose in human serum with no effect by possible interferences on the FIA response.

The use of a mediator serving as an electron donor or acceptor for redox enzymes provides several advantages for electrochemical detection. For example, the mediator permits the enzymatic reaction to proceed independently of oxygen tension. In addition, in the case of glucose detection, electrochemical detection of the mediator can be performed at a lower overvoltage than the oxidation of hydrogen peroxide thereby decreasing the effects of potential interfering species. Generally, incorporation of the mediator along with the immobilized enzyme leads a simpler FIA, thereby regenerating the mediator and the enzyme at the site of enzymatic reaction.

The mediated mechanism of the electrode response may be represented by the following reaction scheme:

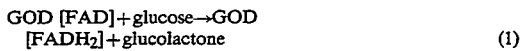
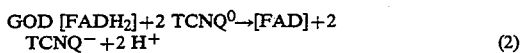

where GOD [FAD] and GOD [FADH$_2$] are the oxidized and reduced forms of glucose oxidase respectively.

Incorporation of enzymes or mediators into carbon paste electrode has been found to result in enhanced mechanical and electrochemical stability with low background current. Since TCNQ acts as an efficient mediator and the redox couple TCNQ$^0$/TCNQ$^-$ is least soluble in aqueous solution, it is of interest to incorporate TCNQ and GOD into the graphite paste.

The biosensor of the present invention includes an enzyme electrode which is used as a working electrode in an electrochemical cell arrangement together with a reference electrode and, preferably, an auxiliary electrode. The arrangement of the electrodes can conform to any standard cell design, including a batch-type cell or a flow-through cell. Moreover, the manner in which potentials are applied and measurements taken, that is how the biosensor is used, are conventional as will be understood from the description below.

The biosensor of the present invention has a number of unique characteristics which are distinguishable over biosensors developed heretofore when used in a batch-type electrochemical cell. For example, the biosensor of the present invention has been found to be extremely stable as compared to previous biosensors.

When used in a flow-injection analysis system, a biosensor developed according to the present invention was found to provide a stable response for 800 consecutive sample injections. In addition, the biosensor for the FIA system was found to have a detection limit of 200 nmol when using a sample volume of 100 µl with an injection loop of 250 µl.

The unique properties and characteristics of the biosensor of the present invention are attributed to the homogeneous composition of the enzyme electrode, the particle size of the graphite paste and the density of the mineral oil used. The enzyme electrode is made from a particular mixture of glucose oxidase (GOD), tetracyanoquinodimethane (TCNQ), graphite powder and a mineral oil which is supported in a suitable holder or electrode body.

According to the present invention, it has been discovered that the superior properties and characteristics of the biosensor can be obtained using an enzyme electrode having a composition of between about 8 to 15 weight percent GOD, between about 28 to 35 weight percent TCNQ, between about 28 to 35 weight percent graphite powder and between about 23 to 30 weight percent of a mineral oil. In a preferred embodiment, the composition of the enzyme electrode was between about 9 to 12 weight percent GOD, between about 30 to 33 weight percent TCNQ, between about 30 to 33 weight percent graphite powder and between about 24 to 28 weight percent of a mineral oil. In a more preferred embodiment, the composition of the enzyme electrode was about 10.76 weight percent GOD, about 31.34 weight percent TCNQ, about 31.34 weight percent graphite powder and about 26.56 weight percent of a mineral oil.

The average particle size of the graphite powder should be less than 10μ and preferably about 1–2μ when the sensor is to be used in a FIA system. The density of the mineral oil should be between about 0.83 to 0.85 g/mL, and preferably about 0.838 g/mL when the sensor is used in a FIA system.

The electrode is formed by blending the GOD, TCNQ, graphite powder and mineral oil together to form a homogeneous paste and then loading the paste into an inert, e.g., plastic, support which includes an electrical lead that provides an electrical connection to the paste. The support or body also provides for the paste to have an exposed surface for contacting the enzyme electrode to a sample fluid. Such electrode supports are known in the art and in their simplest designs involve merely wells or bores that are formed in the surface of an inert material support.

FIG. 1 is a schematic diagram of a biosensor according to the present invention. The basic enzyme electrode 1 used in the biosensor of the present invention was made by pressing the active paste mixture 2 into a well 3 of an electrode body 4 made from Teflon. The paste surface 5 was manually smoothed on clean paper. The paste 2 was prepared by mixing of graphite fine powder and TCNQ in a mortar followed by the addition of GOD and Nujol oil. According to a preferred embodiment, the mineral oil was Nujol oil and the well 3 had a diameter of 3 mm and a depth of 2 mm. The electrode body 4 serves to support the enzyme electrode and can be of any convenient shape including cylindrical, rectangular, etc. In FIG. 1, an electrical lead 6 is illustrated as being in contact with the active paste 2.

The graphite paste enzyme electrode modified with TCNQ according to the present invention has high storage and operational stability as compared to earlier carbon paste glucose electrodes and offers significant advantages in handling along with the ability for miniaturization of the probes.

The biosensor which uses the enzyme electrode described above can be used in a batch-type electrochemical cell. However, the utility of the biosensor can perhaps best be exploited by incorporating the biosensor into a flow-injection analysis system as described hereafter.

Because of the dynamic conditions which exist in FIA systems, leaching of the TCNQ from the enzyme electrode is more likely to occur in a FIA system than in a batch-type electrochemical cell. Accordingly, the composition of the enzyme electrode becomes more critical when used in a FIA system. Therefore, in order to achieve a wide linear dynamic range and good mechanical and electrochemical stability, the preferred compositions of the enzyme electrode which are discussed above are used when the enzyme electrode is incorporated into a FIA system. These include: a composition of about 10.76 weight percent GOD, about 31.34 weight percent TCNQ, about 31.34 weight percent graphite powder and about 26.56 weight percent of a mineral oil, wherein the graphite powder has a particle size of 1–2μ and the density of the mineral oil (Nujol oil) is about 0.838 g/mL.

Figure 4:
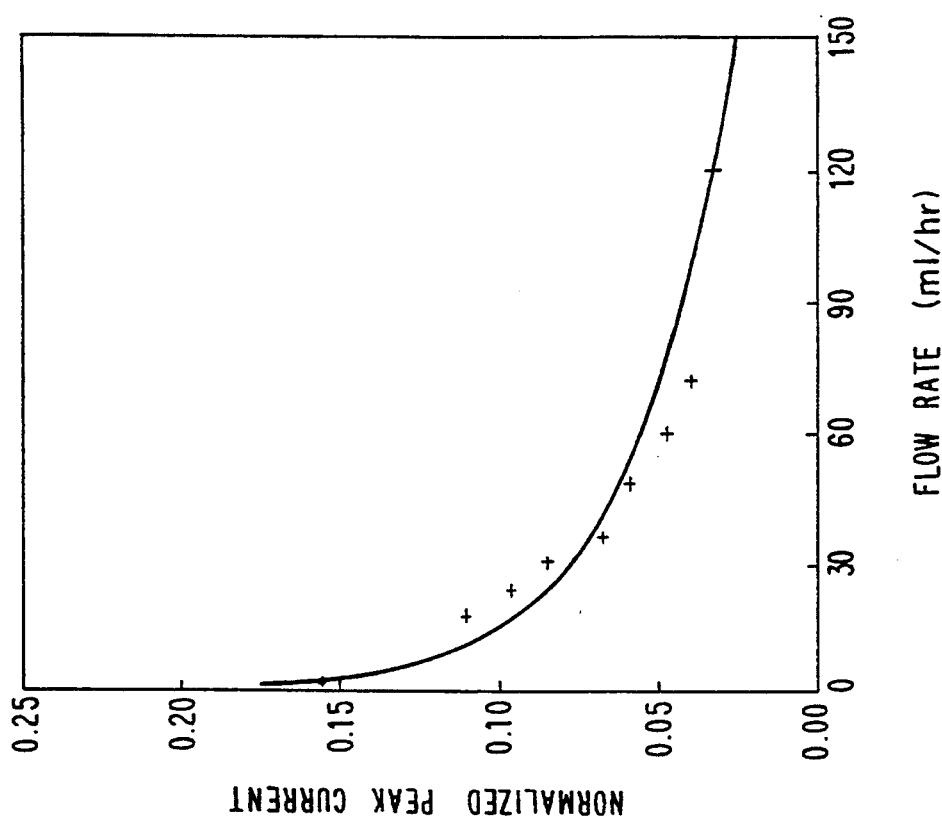
FIG. 4 is a plot which shows the effects of flow rates on flow-injection response peaks.

FIG. 4 is a diagram of a flow injection system according to one embodiment of the present invention. The flow injection system includes a pump 10, e.g. a peristaltic pump, which can be operated to supply a carrier fluid to the enzyme sensor 11 which is provided in a conventional electrochemical flow cell having a reference electrode, and an auxiliary electrode (not shown). A sample injector 12 is provided which in-line between the pump 10 and the enzyme sensor 11. The sample injector includes a conventional sample loop for measuring sample volumes that are injected into the flow line between the pump 10 and the enzyme sensor 11.

The following examples are given to illustrate various features and characteristics of the biosensor of the present invention which is not to be considered as being limited thereto. In the examples and throughout, percentages are by weight unless otherwise indicated.

EXAMPLE 1

An enzyme electrode for an FIA system was prepared by pressing active graphite based paste into an electrode body (MF-1004) for the LC-17A flow-cell (Bioanalytical System, Inc.; West Lafayette, Ind.). Each electrode body had two wells which were 3 mm in diameter and 3 cm deep. Two thirds of each well was filled with a graphite based paste composed of 73 weight percent Graphite powder and 27 weight percent mineral oil. The remaining one third of the well was filled with active paste composed of 31.34 weight percent Graphite powder, 31.34 weight percent TCNQ, 26.56 weight percent mineral oil, and 10.76 weight percent GOD. After the wells were filled, the paste surface was manually smoothed on clean paper. Before placing the electrode into the flow cell, it was covered with a nucleopore membrane (polycarbonate membrane filters, 0.1 μm).

A phosphate buffer (0.1M, pH 7.0) was pumped by a peristaltic pump (Waters 501 HPLC pump, Waters, Milford, Mass.) to the flow cell through an injector (Waters model U6K). A 100 μl sample was introduced, unless otherwise stated, through the injector which was equipped with a 250 μl sample loop. The injector was connected to the flow cell through a stainless steel inlet tubing. The flow rate was 30 ml/h unless otherwise stated. The electrode potential was controlled with a potentiostat (Pine Instrument Co., Grove city, Pa., model AFRDE4) and the electrode responses were recorded with a linear recorder (model 1200, Reno, Nev.).

The enzyme electrode was maintained at 200 mV vs Ag/AgCl. Before using a new electrode, an 80 mM glucose solution in 0.1M phosphate buffer pH 7 was continuously circulated through the flow cell for at least 5 hours at 30 ml/hr. The temperature of the carrier buffer stream was regulated with a Brookfield thermostat (Stoughton, Mass).

EXAMPLE 2

Figure 3:
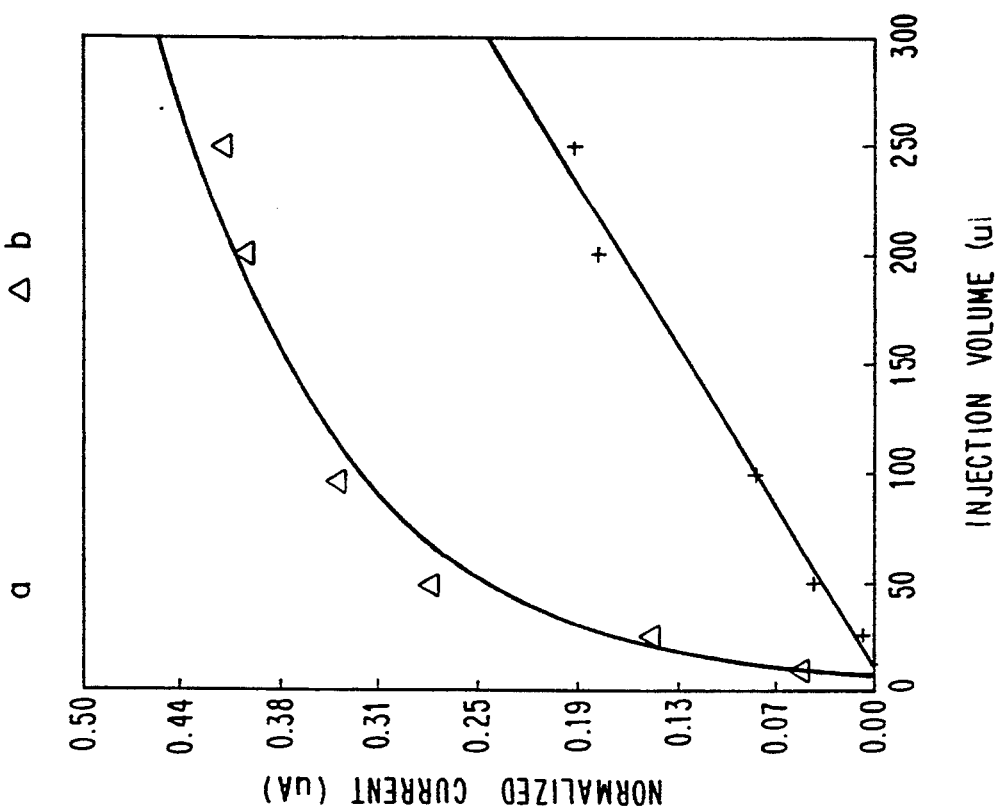
FIG. 3 is a plot which shows the effects of injection volume on flow-injection response peaks.

In this example, the FIA system of Example 1 was tested to investigate the effect of injection volume on the response of the FIA biosensor. For this example, the injector was fitted with an injection sample loop of 250 μl. The results are plotted in FIG. 3. As can be seen from FIG. 3, there was an increase in response with increasing injection volume. This is in accordance with previous observations on a diffusion-limited amperometric enzyme electrode in an FIA system (Olsson et al, Anal. Chem., 58, 1046 (1986). The response increased linearly with increasing sample volume, at a low concentration of glucose 8 μmol/100 μl (FIG. 3, curve a) as compared to when a higher concentration of glucose 50 μmol/100 μl (FIG. 3, curve b), is injected. Considering the low injection volume and sensitivity of the sensor, a 100 μl sample injection volume was chosen for further measurements.

EXAMPLE 3

In this example the effect of flow rate on the response of the FIA biosensor was investigated. The above FIA system was tested at different flow rates. The results of these tests are shown in FIG. 4. The data shows the normalized peak height FIA response for the injection of 8 μmol/100 μl glucose as a function of flow rate. The peak height was normalized with respect to steady-state responses of the sensor at a flow rate of 30 ml/h. As can be seen from FIG. 4, the response of the FIA sensor decreases on increasing the flow rate which is in accordance with the theoretical prediction for a FIA system (Olsson et al, *Anal. Chem.*, 58, 1046 (1986). As a compromise between sensitivity and throughput, a flow rate of 30 ml/h was selected for further experiments.

The effect of pH on the response of the FIA biosensor was also studied. The results suggested that response is nearly constant within the physiological pH range (6.8 to 8).

EXAMPLE 4

Figure 5:
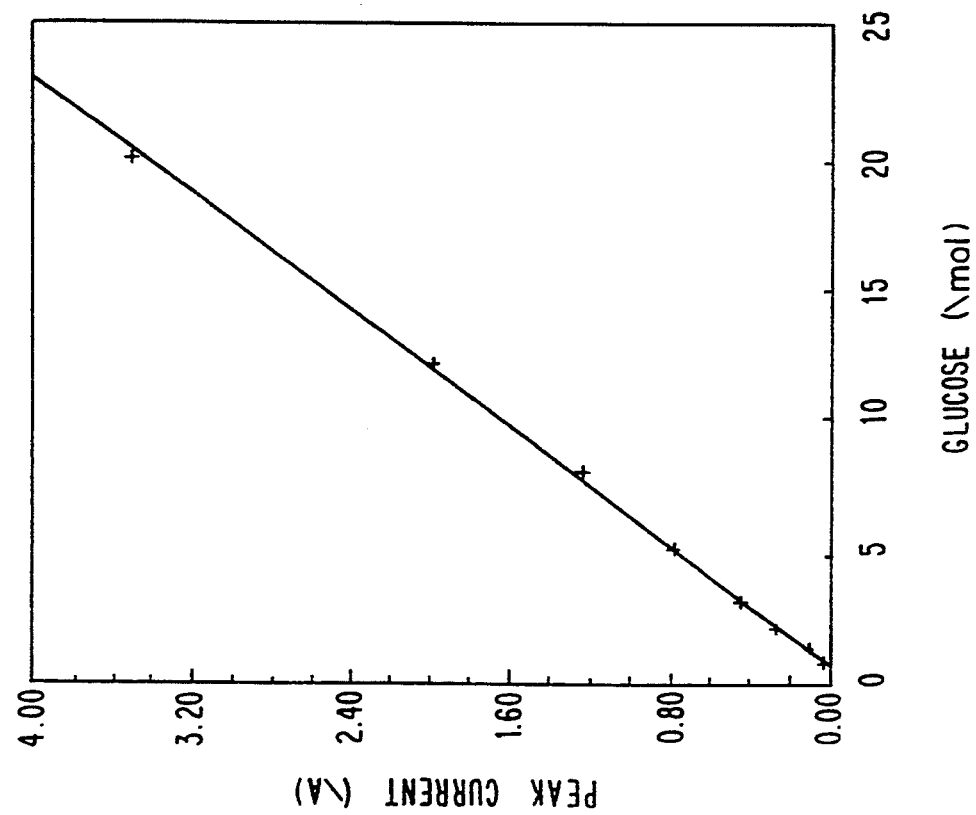
FIG. 5 is a glucose calibration assay for the flow-injection analysis system according to the present invention.

In this example, glucose analysis was performed using the FIA system. It was found that biosensor produced an excellent linear response to glucose up to 20 μmol/100 μl in peak height mode. Each assay took 3 min with a throughput of 20/h. FIG. 5 shows a calibration curve for the analysis of glucose with a 100 μl sample at a flow rate of 30 ml/h. The lowest detection limit was 200 nmol/100 μl with a wide linearity up to 20 μmol/100 μl. The sensitivity of the biosensor was determined to be 17.6±0.016 μA/100 μmol (99% confidence interval, n=9, correlation coefficient=0.998).

EXAMPLE 5

Figure 6:
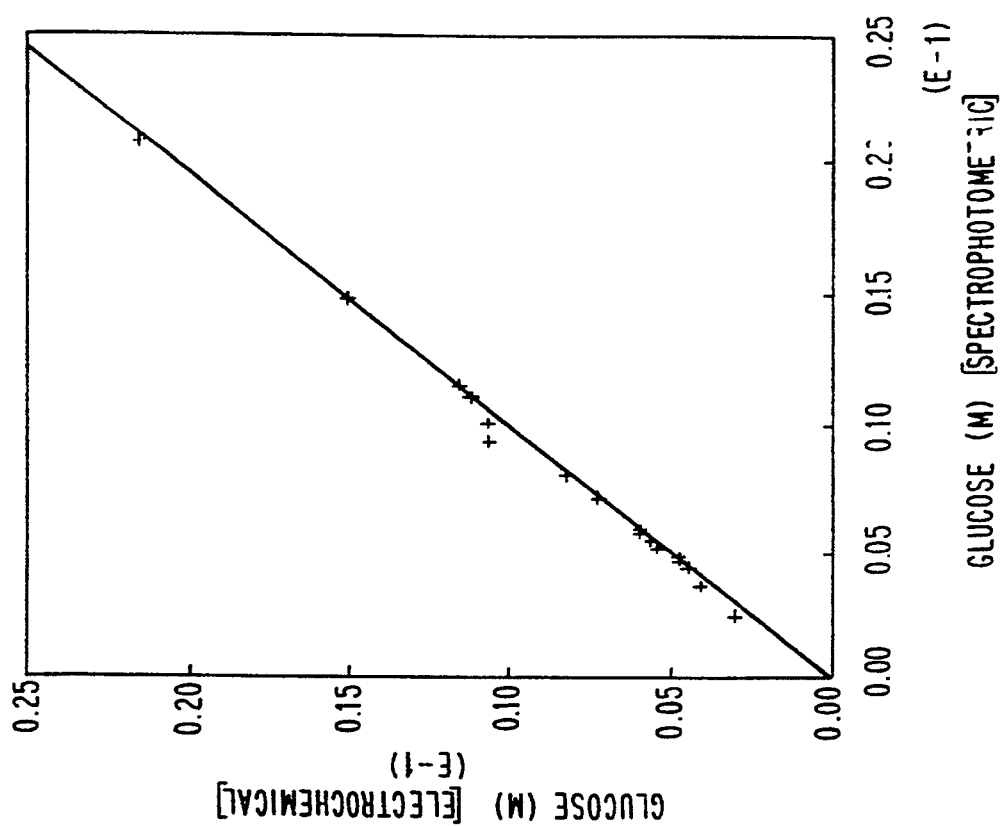
FIG. 6 is a plot of glucose plasma analysis utilizing a flow-injection analysis biosensor according to the present invention and routine spectrophotometric analysis.

In this example, the FIA biosensor was used to analyze glucose in human serum samples. The serum samples (100 μl) were injected into the system at a flow rate of 30 ml/h. The results obtained by this method (Y) and those by a commercial spectrophotometric method (X) are plotted in FIG. 6. There is an excellent linearity between these two sets of data. Least squares analysis of the relationship between the two methods is Y=1.022±0.00017M (correlation coefficient=0.986, n=19). This demonstrates the accuracy of the biosensor used in the FIA system.

EXAMPLE 6

Figure 7:
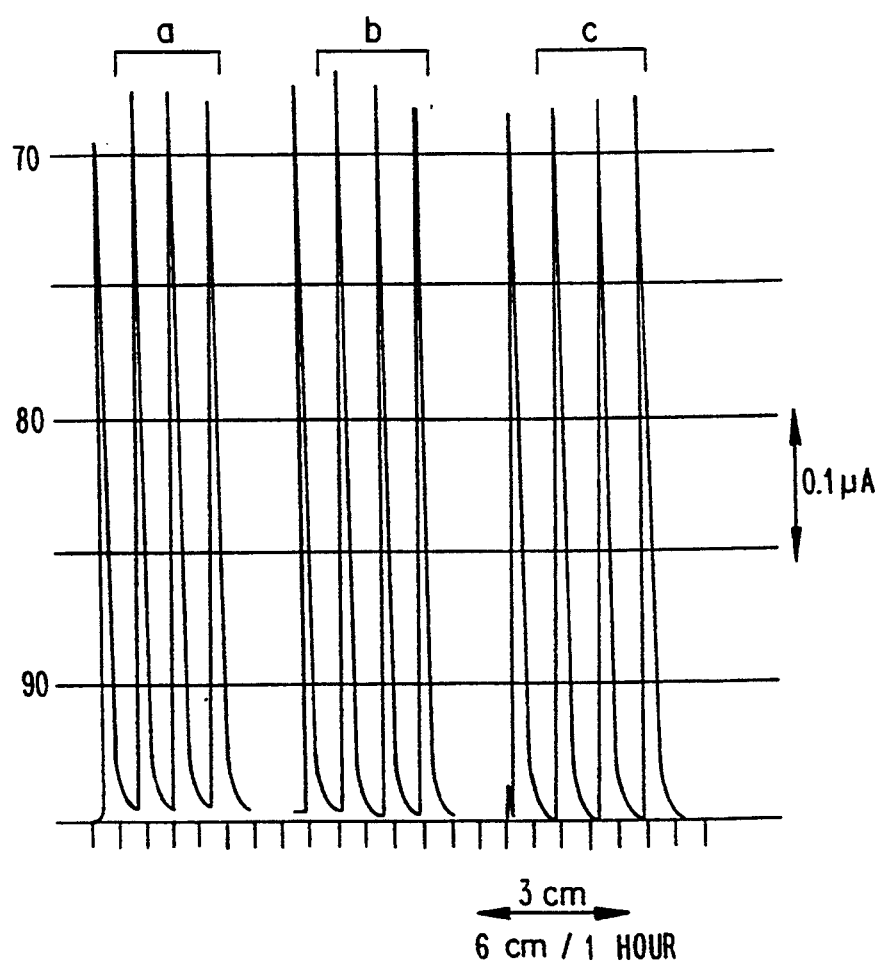
FIG. 7 is a plot which shows the effects of ascorbic acid and acetaminophen on flow-injection response peaks.

In this example, the effect of major interferences (ascorbic acid and acetaminophen) on the response of the FIA glucose biosensor were studied. The results of this example are presented in FIG. 7 which shows the results of the injection of 100 μl glucose stock solution in absence of interferences (a), presence of ascorbic acid (0.15 mM) (b) and presence of acetaminophen (0.25 mM). As can be seen, the response of the glucose biosensor was not affected by these interferences on the injection of 100 μl samples.

The stability of the FIA glucose sensor was studied by continuous (800) injections of 8 μmol glucose. There was a decrease in sensitivity by 15% by the 800th sample.

Although the invention has been described with reference to particular means, materials and embodiments, from the foregoing description, one skilled in the art can easily ascertain the essential characteristics of the present invention and various changes and modifications may be made to adapt the various usages and conditions without departing from the spirit and scope of the present invention as described in the claims which follow.

I claim:

1. An electrode for a biosensor which comprises a homogeneous composition of between about 8 to 15 weight percent of a redox enzyme, between about 28 to 35 weight percent of an electron-transfer mediator, between about 28 to 35 weight percent graphite powder, and between about 23 to 30 weight percent of a mineral oil.

2. An electrode for a biosensor according to claim 1, wherein said redox enzyme comprises glucose oxidase.

3. An electrode for a biosensor according to claim 2 wherein said electron-transfer mediator comprises tetracyanoquinodimethane.

4. An electrode for a biosensor according to claim 2 wherein said mineral oil is Nujol oil.

5. An electrode for a biosensor according to claim 2, wherein said mineral oil has a density of between about 0.83 and 0.85 g/mL.

6. An electrode for a biosensor according to claim 2, wherein said graphite powder has a particle size of less than 10 microns.

7. An electrode for a biosensor according to claim 1, wherein said composition is held in a support.

8. In a flow-injection analysis system comprising a pump, an electrochemical cell, a flow line connected between said pump and said electrochemical cell and a sample injector connected to said flow line, the improvement comprising an enzyme electrode for said electrochemical cell which comprises a homogeneous composition of between about 9 to 12 weight percent of a redox enzyme, between about 30 to 33 weight percent of an electron-transfer mediator, between about 30 to 33 weight percent graphite powder, and between about 24 to 28 weight percent of a mineral oil.

9. A flow-injection analysis system according to claim 8, wherein said redox enzyme comprises glucose oxidase.

10. A flow-injection analysis system according to claim 9, wherein said electron-transfer mediator comprises tetracyanoquinodimethane.

11. A flow-injection analysis system according to claim 9, wherein said mineral oil comprises Nujol oil.

12. A flow-injection analysis system according to claim 9, wherein said mineral oil has a density of between about 0.83 and 0.85 g/mL.

13. A flow-injection analysis system according to claim 12, wherein said mineral oil has a density of about 0.838 g/mL.

14. A flow-injection analysis system according to claim 9, wherein said graphite powder has a particle size of less than 10 microns.

15. A flow-injection analysis system according to claim 14, wherein said graphite powder has a particle size of between 1-2 microns.

16. A flow-injection analysis system according to claim 8, wherein said composition is held in a support.

17. A method of measuring glucose concentration in a sample which comprises:

providing a sample fluid containing glucose;

providing an electrochemical cell having a working electrode which comprises a homogeneous composition of between about 8 to 15 weight percent of glucose oxidase, between about 28 to 35 weight percent of tetracyanoquinodimethane, between about 28 to 35 weight percent graphite powder and between about 23 to 30 weight percent of mineral oil;

supplying said sample fluid to said electrochemical cell; and measuring glucose concentration in said sample fluid by means of said electrochemical cell.

18. A method of measuring glucose concentration in a sample according to claim 17, wherein said electrochemical cell comprises a flow cell and said sample fluid is supplied to said electrochemical cell by means of a flow-injection system.

19. A method of measuring glucose concentration in a sample according to claim 17, wherein said sample comprises blood serum.

* * * * *